United States Patent
Shafe et al.

(10) Patent No.: US 9,328,038 B2
(45) Date of Patent: May 3, 2016

(54) HIGH TEMPERATURE QUENCH SYSTEM AND PROCESS

(71) Applicant: UOP LLC, Des Plaines, IL (US)

(72) Inventors: Peter Shafe, Chicago, IL (US); Aziz Sattar, West Chicago, IL (US); Mohammad Reza Mostofi-Ashtiani, Naperville, IL (US); Laura E. Leonard, Western Springs, IL (US); Rajeswar Gattupalli, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 182 days.

(21) Appl. No.: 14/316,140

(22) Filed: Jun. 26, 2014

(65) Prior Publication Data

US 2015/0000313 A1    Jan. 1, 2015

Related U.S. Application Data

(60) Provisional application No. 61/841,272, filed on Jun. 28, 2013.

(51) Int. Cl.
*C07C 2/78* (2006.01)
*F28D 21/00* (2006.01)

(52) U.S. Cl.
CPC ........... *C07C 2/78* (2013.01); *F28D 2021/0059* (2013.01)

(58) Field of Classification Search
CPC .............. C07C 2/78; F28D 2021/0019; F28D 2021/0059
See application file for complete search history.

(56) References Cited

U.S. PATENT DOCUMENTS

| 4,188,796 A * | 2/1980 | Raab ......................... F28C 3/06 208/101 |
| 4,387,263 A | 6/1983 | Vogt |
| 4,587,373 A | 5/1986 | Hsia |
| 5,020,335 A * | 6/1991 | Albers ..................... B01D 1/14 D1/14 |
| 5,095,163 A | 3/1992 | Barger |
| 5,126,308 A | 6/1992 | Barger |
| 5,191,141 A | 3/1993 | Barger |
| 5,219,530 A * | 6/1993 | Hertzberg ............ G10K 15/043 208/128 |
| 7,183,451 B2 | 2/2007 | Gattis |
| 2004/0068137 A1* | 4/2004 | Herold .................. C07C 263/10 560/347 |
| 2012/0273175 A1* | 11/2012 | Blanchard ................ C10K 1/04 165/157 |
| 2015/0000323 A1* | 1/2015 | Shafe ........................ C07C 2/76 62/310 |

FOREIGN PATENT DOCUMENTS

| EP | 0045062 A1 | 2/1982 |
| JP | 2004101060 A | 4/2004 |
| KR | 1020030067241 A | 8/2003 |

OTHER PUBLICATIONS

PCT International Search Report for PCT/US2014/044317, mailing date Oct. 20, 2014.
U.S. Appl. No. 14/316,113, filed Jun. 26, 2014.

* cited by examiner

*Primary Examiner* — Daniel Rohrhoff

(57) ABSTRACT

A quench system and process for cooling high temperature gases is presented. The quench system includes a frustum, or conic, shaped section having an inlet at the smaller end of the quench section and the outlet at the larger end of the quench section. The system includes spray nozzles having openings flush with the wall of the quench section. The process includes spraying a large volume of liquid in small droplets for rapid heat transfer and vaporization of the quench liquid.

20 Claims, 5 Drawing Sheets

US 9,328,038 B2

HIGH TEMPERATURE QUENCH SYSTEM AND PROCESS

CROSS REFERENCE TO RELATED APPLICATION

This application claims the benefit of U.S. Provisional Application No. 61/841,272 which was filed on Jun. 28, 2013, the contents of which are hereby incorporated by reference in its entirety.

FIELD OF THE INVENTION

An apparatus and process are disclosed for the quenching of hot reactor fluids. In particular, the quenching of a hot reactor effluent from a supersonic flow reactor.

BACKGROUND OF THE INVENTION

Light olefin materials, including ethylene and propylene, represent a large portion of the worldwide demand in the petrochemical industry. Light olefins are used in the production of numerous chemical products via polymerization, oligomerization, alkylation and other well-known chemical reactions. These light olefins are essential building blocks for the modern petrochemical and chemical industries. Producing large quantities of light olefin material in an economical manner, therefore, is a focus in the petrochemical industry. The main source for these materials in present day refining is the steam cracking of petroleum feeds.

The cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production. In a typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier byproducts that tend to foul the pyrolysis tube walls. However, there is little room left to improve the residence times or overall energy consumption in traditional pyrolysis processes.

More recent attempts to decrease light olefin production costs include utilizing alternative processes and/or feed streams. In one approach, hydrocarbon oxygenates and more specifically methanol or dimethylether (DME) are used as an alternative feedstock for producing light olefin products.

Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once the oxygenates are formed, the process includes catalytically converting the oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. U.S. Pat. No. 4,587,373 discloses using a zeolitic catalyst like ZSM-5 for purposes of making light olefins. U.S. Pat. Nos. 5,095,163; 5,126,308 and 5,191,141 on the other hand, disclose an MTO conversion technology utilizing a non-zeolitic molecular sieve catalytic material, such as a metal aluminophosphate (ELAPO) molecular sieve. OTO and MTO processes, while useful, utilize an indirect process for forming a desired hydrocarbon product by first converting a feed to an oxygenate and subsequently converting the oxygenate to the hydrocarbon product. This indirect route of production is often associated with energy and cost penalties, often reducing the advantage gained by using a less expensive feed material.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel. While this method may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

While the foregoing traditional pyrolysis systems provide solutions for converting ethane and propane into other useful hydrocarbon products, they have proven either ineffective or uneconomical for converting methane into these other products, such as, for example ethylene. While MTO technology is promising, these processes can be expensive due to the indirect approach of forming the desired product. Due to continued increases in the price of feeds for traditional processes, such as ethane and naphtha, and the abundant supply and corresponding low cost of natural gas and other methane sources available, for example the more recent accessibility of shale gas, it is desirable to provide commercially feasible and cost effective ways to use methane as a feed for producing ethylene and other useful hydrocarbons.

SUMMARY OF THE INVENTION

A process for quenching a high temperature and high speed flow is presented. The process includes passing a high speed vapor flow into a quench section. A liquid is sprayed into the quench section, wherein the liquid has a high heat of vaporization, and the liquid is sprayed into the quench section with droplets having a mean diameter less than 500 micrometers. The quench section has a frustum shape, or a conic shape, with a diverging system, such that the flow at the vapor slows. The liquid is sprayed through at least one nozzle embedded in the quench section wall and has a nozzle outlet that is substantially flush with the quench section wall.

Other objects, advantages and applications of the present invention will become apparent to those skilled in the art from the following detailed description and drawings.

DETAILED DESCRIPTION OF THE INVENTION

One proposed alternative to the previous methods of producing olefins that has not gained much commercial traction includes passing a hydrocarbon feedstock into a supersonic reactor and accelerating it to supersonic speed to provide kinetic energy that can be transformed into heat to enable an endothermic pyrolysis reaction to occur. Variations of this process are set out in U.S. Pat. Nos. 4,136,015 and 4,724,272, and Russian Patent No. US 392723A. These processes include combusting a feedstock or carrier fluid in an oxygen-rich environment to increase the temperature of the feed and accelerate the feed to supersonic speeds. A shock wave is created within the reactor to initiate pyrolysis or cracking of the feed.

More recently, U.S. Pat. Nos. 5,219,530 and 5,300,216 have suggested a similar process that utilizes a shock wave reactor to provide kinetic energy for initiating pyrolysis of natural gas to produce acetylene. More particularly, this process includes passing steam through a heater section to become superheated and accelerated to a nearly supersonic speed. The heated fluid is conveyed to a nozzle which acts to expand the carrier fluid to a supersonic speed and lower temperature. An ethane feedstock is passed through a compressor and heater and injected by nozzles to mix with the supersonic carrier fluid to turbulently mix together at a speed of about Mach 2.8 and a temperature of about 427 C. The temperature in the mixing section remains low enough to restrict premature pyrolysis. The shockwave reactor includes a pyrolysis section with a gradually increasing cross-sectional area where a standing shock wave is formed by back pressure in the reactor due to flow restriction at the outlet. The shock wave rapidly decreases the speed of the fluid, correspondingly rapidly increasing the temperature of the mixture by converting the kinetic energy into heat. This immediately initiates pyrolysis of the ethane feedstock to convert it to other products. A quench heat exchanger then receives the pyrolized mixture to quench the pyrolysis reaction.

Methods and apparatus for converting hydrocarbon components in methane feed streams using a supersonic reactor are generally disclosed. As used herein, the term "methane feed stream" includes any feed stream comprising methane. The methane feed streams provided for processing in the supersonic reactor generally include methane and form at least a portion of a process stream. The apparatus and methods presented herein convert at least a portion of the methane to a desired product hydrocarbon compound to produce a product stream having a higher concentration of the product hydrocarbon compound relative to the feed stream.

Figure 2:
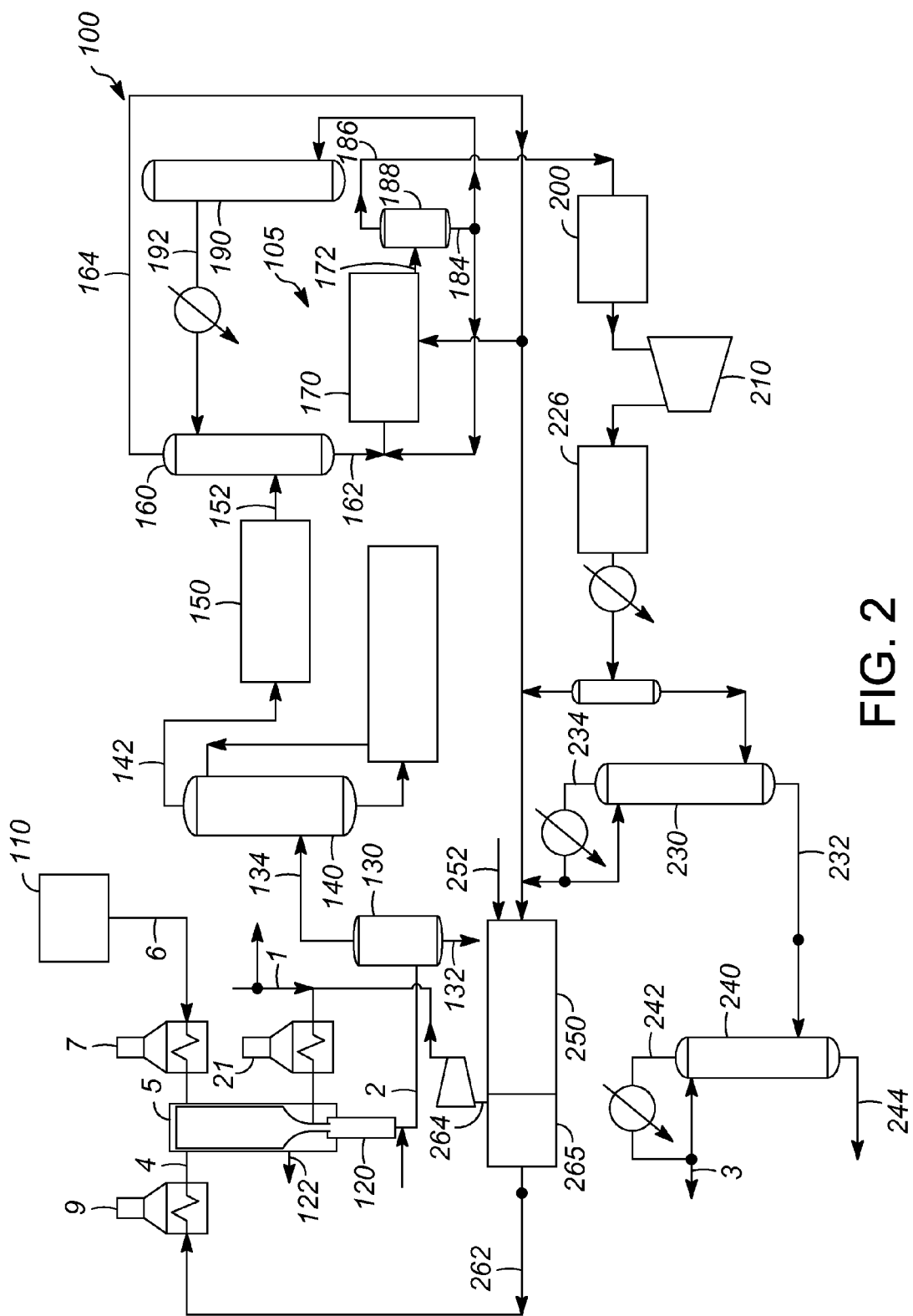
FIG. 2 is a schematic view of a system for converting methane into acetylene and other hydrocarbon products in accordance with various embodiments described herein.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such hydrocarbon stream. The "hydrocarbon stream" may include the methane feed stream, a supersonic reactor effluent stream, a desired product stream exiting a downstream hydrocarbon conversion process or any intermediate or by-product streams formed during the processes described herein. The hydrocarbon stream may be carried via a process stream line 115, as shown in FIG. 2, which includes lines for carrying each of the portions of the process stream described above. The term "process stream" as used herein includes the "hydrocarbon stream" as described above, as well as it may include a carrier fluid stream, a fuel stream, an oxygen source stream, or any streams used in the systems and the processes described herein. The process stream may be carried via a process stream line 125, which includes lines for carrying each of the portions of the process stream described above.

A more full description of FIG. 2 includes passing the oxygen source from and air separation unit 110, preheating the oxygen source in the heater 7 and passing the oxygen to the supersonic reactor 5. A fuel source 4 can be preheated in a heater 9 and passed to the reactor 5. The methane 1 is passed to a heater 21 and passed into the supersonic flow section of the reactor 5. This generates the process stream which is then quenched in a quench section 120 to rapidly cool the reactants. The quench can be with water for con-current steam generation 122. The reactor effluent stream 2, having been quenched is passed to a knock-out drum 130 to separate a water stream 132 comprising water and soot, and a cooled process stream 134 comprising hydrocarbons. The process stream 134 can be passed to an absorber 140 to recover and recycle methane and to removed oxygenates to generate a partially cleaned process stream 142. The cleaned process stream 142 is passed to a compressor 150 to generate a compressed product stream 152. The compressed product stream 152 is passed to an absorber 160 to absorb the acetylene to generate a bottoms stream 162 comprising acetylene and solvent, and an overhead stream 164 comprising other hydrocarbons. The bottoms stream 162 is passed to a hydrogenation unit 170 to generate a process stream 172 comprising ethylene. The ethylene process stream 172 is passed to a separation unit 180 to generate an ethylene overhead stream 182 and a bottoms stream 184 comprising solvent. The solvent stream 184 is passed to a solvent regenerator 190 to provide a solvent stream 192 to the acetylene absorber 160. The ethylene overhead stream 182 is passed to a contaminant removal zone 200 to generate an ethylene stream 202 with reduced contaminants. The ethylene stream 202 is compressed 210 and dried 220 and passed to a demethanizer column 230 to generate an ethylene bottoms stream 232 and a light gas overhead stream 234. The ethylene stream 232 is passed to a deethanizer column 240 to generate an ethylene overhead product stream 242 and a heavier hydrocarbon bottoms stream 244 for recycle. The demethanizer overhead stream 234 is passed to a water gas shift reactor 250 with a stream 252 to generate a water gas shift stream comprising hydrogen. The water gas shift stream is passed to a pressure swing absorber 260 to generate a hydrogen stream 262 for use in the supersonic reactor 5, and a second stream 264 comprising methane and other gases. The second stream 264 can be compressed and recycled for use in the feedstream.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offers significant improvement over traditional pyrolysis processes. It has more recently been realized that these processes may also be able to convert methane to acetylene and other useful hydrocarbons, whereas more traditional pyrolysis processes were incapable or inefficient for such conversions.

The majority of previous work with supersonic reactor systems, however, has been theoretical or research based, and thus has not addressed problems associated with practicing the process on a commercial scale. In addition, many of these prior disclosures do not contemplate using supersonic reactors to effectuate pyrolysis of a methane feed stream, and tend to focus primarily on the pyrolysis of ethane and propane. One problem that has recently been identified with adopting the use of a supersonic flow reactor for light alkane pyrolysis, and more specifically the pyrolysis of methane feeds to form acetylene and other useful products therefrom, includes effectively quenching the hot stream in the supersonic reactor. More particularly, as described below, if the methane is heated above a pyrolysis temperature for too long, the pyrolysis reaction may continue converting a large portion of the feed into unwanted products, such as coke or soot. Thus, it is desired to effectively cool the stream after it has reacted the pyrolysis temperature. This is further made difficult due to the very high temperatures present in the supersonic reactor. Because temperatures in the reactor may reach 3000 C and higher, it may be difficult to quickly and effectively cool the fluid. Further, the high temperatures and supersonic flowrates present in the reactor chamber may cause melting or other deterioration of any equipment, including nozzles, used for quenching the stream.

More specifically, the carrier stream and feed stream may travel through the reactor at supersonic speeds, which can quickly erode many materials that could be used to form the equipment used for quenching. Moreover, certain substances and contaminants that may be present in the hydrocarbon stream can cause corrosion, oxidation, and/or reduction of the reactor walls or shell and other equipment or components of the reactor. Such components causing corrosion, oxidation, or reduction problems may include, for example hydrogen sulfide, water, methanethiol, arsine, mercury vapor, carbidization via reaction with the fuel itself, or hydrogen embrittlement.

In accordance with various embodiments disclosed herein, therefore, apparatus and methods for converting methane in hydrocarbon streams to acetylene and other products is provided. Apparatus in accordance herewith, and the use thereof, have been identified to improve the overall process for the pyrolysis of light alkane feeds, including methane feeds, to acetylene and other useful products. The apparatus and processes described herein also beneficially improve the ability to effectively decrease the temperature of the stream passing through the supersonic reactor to control the pyrolysis reaction occurring therein and further provides for the apparatus and associated components and equipment of the quench process to withstand degradation and possible failure due to extreme operating conditions within the reactor.

In accordance with one approach, the apparatus and methods disclosed herein are used to treat a hydrocarbon process stream to convert at least a portion of methane in the hydrocarbon process stream to acetylene. The hydrocarbon process stream described herein includes the methane feed stream provided to the system, which includes methane and may also include ethane or propane. The methane feed stream may also include combinations of methane, ethane, and propane at various concentrations and may also include other hydrocarbon compounds as well as contaminants. In one approach, the hydrocarbon feed stream includes natural gas. The natural gas may be provided from a variety of sources including, but not limited to, gas fields, oil fields, coal fields, fracking of shale fields, biomass, and landfill gas. In another approach, the methane feed stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The methane feed stream may include a stream from combinations of different sources as well.

In accordance with the processes and systems described herein, a methane feed stream may be provided from a remote location or at the location or locations of the systems and methods described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation methods. For example a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 65 mol-% to about 100 mol-%. In another example, the concentration of methane in the hydrocarbon feed ranges from about 80 mol-% to about 100 mol-% of the hydrocarbon feed. In yet another example, the concentration of methane ranges from about 90 mol-% to about 100 mol-% of the hydrocarbon feed.

In one example, the concentration of ethane in the methane feed ranges from about 0 mol-% to about 35 mol-% and in another example from about 0 mol-% to about 10 mol-%. In one example, the concentration of propane in the methane feed ranges from about 0 mol-% to about 5 mol-% and in another example from about 0 mol-% to about 1 mol-%.

The methane feed stream may also include heavy hydrocarbons, such as aromatics, paraffinic, olefinic, and naphthenic hydrocarbons. These heavy hydrocarbons if present will likely be present at concentrations of between about 0 mol-% and about 100 mol-%. In another example, they may be present at concentrations of between about 0 mol-% and 10 mol-% and may be present at between about 0 mol-% and 2 mol-%.

The apparatus and method for forming acetylene from the methane feed stream described herein utilizes a supersonic flow reactor for pyrolyzing methane in the feed stream to form acetylene. The supersonic flow reactor may include one or more reactors capable of creating a supersonic flow of a carrier fluid and the methane feed stream and expanding the carrier fluid to initiate the pyrolysis reaction. In one approach, the process may include a supersonic reactor as generally described in U.S. Pat. No. 4,724,272, which is incorporated herein by reference, in its entirety. In another approach, the process and system may include a supersonic reactor such as described as a "shock wave" reactor in U.S. Pat. Nos. 5,219,530 and 5,300,216, which are incorporated herein by reference, in their entirety. In yet another approach, the supersonic reactor described as a "shock wave" reactor may include a reactor such as described in "Supersonic Injection and Mixing in the Shock Wave Reactor" Robert G. Cerff, University of Washington Graduate School, 2010.

Figure 1:
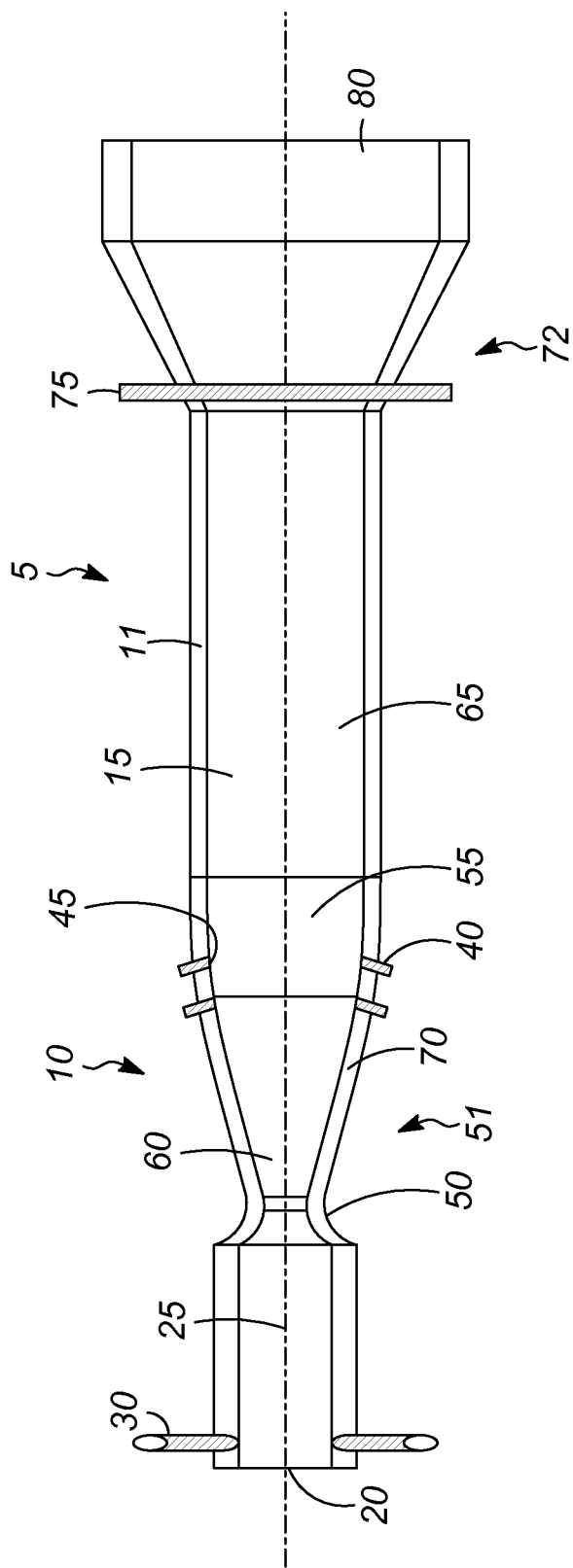
FIG. 1 is a side cross-sectional view of a supersonic reactor in accordance with various embodiments described herein.

While a variety of supersonic reactors may be used in the present process, an exemplary reactor 5 is illustrated in FIG. 1. Referring to FIG. 1, the supersonic reactor 5 includes a reactor vessel 10 generally defining a reactor chamber 15. While the reactor 5 is illustrated as a single reactor, it should be understood that it may be formed modularly or as separate vessels. If formed modularly or as separate components, the modules or separate components of the reactor may be joined together permanently or temporarily, or may be separate from one another with fluids contained by other means, such as, for example, differential pressure adjustment between them. A combustion zone or chamber 25 is provided for combusting a fuel to produce a carrier fluid with the desired temperature and flowrate. The reactor 5 may optionally include a carrier fluid inlet 20 for introducing a supplemental carrier fluid into the reactor. One or more fuel injectors 30 are provided for injecting a combustible fuel, for example hydrogen, into the combustion chamber 25. The same or other injectors may be provided for injecting an oxygen source into the combustion chamber 25 to facilitate combustion of the fuel. The fuel and oxygen are combusted to produce a hot carrier fluid stream typically having a temperature of from about 1200 to about 3500 C in one example, between about 2000 and about 3500 in another example, and between about 2500 and about 3200 C in yet another example. It is also contemplated herein to produce the hot carrier fluid stream by other known methods, including non-combustion methods. According to one example the carrier fluid stream has a pressure of about 1 atm or higher, greater than about 2 atm in another example, and greater than about 4 atm in another example. In one example, the carrier fluid stream has a pressure between 12 and 20 atm.

The hot carrier fluid stream from the combustion zone 25 is passed through a supersonic expander 51 that includes a converging-diverging nozzle 50 to accelerate the flowrate of the carrier fluid to above about mach 1.0 in one example, between about mach 1.0 and mach 4.0 in another example, and between about mach 1.5 and 3.5 in another example. In this regard, the residence time of the fluid in the reactor portion of the supersonic flow reactor is between about 0.5-100 ms in one example, about 1.0-50 ms in another example, and about 1.5-20 ms in another example. The temperature of the carrier fluid stream through the supersonic expander by one example is between about 1000 C and about 3500 C, between about 1200 C and about 2500 C in another example, and between about 1200 C and about 2000 C in another example.

A feedstock inlet 40 is provided for injecting the methane feed stream into the reactor 5 to mix with the carrier fluid. The feedstock inlet 40 may include one or more injectors 45 for injecting the feedstock into the nozzle 50, a mixing zone 55, a diffuser zone 60, or a reaction zone or chamber 65. The injector 45 may include a manifold, including for example a plurality of injection ports or nozzles for injecting the feed into the reactor 5.

In one approach, the reactor 5 may include a mixing zone 55 for mixing of the carrier fluid and the feed stream. In one approach, as illustrated in FIG. 1, the reactor 5 may have a separate mixing zone, between for example the supersonic expander 51 and the diffuser zone 60, while in another approach, the mixing zone is integrated into the diffuser section is provided, and mixing may occur in the nozzle 50, expansion zone 60, or reaction zone 65 of the reactor 5. An expansion zone 60 includes a diverging wall 70 to produce a rapid reduction in the temperature of the gases flowing therethrough, to convert the thermal energy of the flowing fluid to kinetic energy to further heat the stream to cause pyrolysis of the methane in the feed, which may occur in the expansion section 60 and/or a downstream reaction section 65 of the reactor. The fluid is quickly quenched in a quench zone 72 to stop the pyrolysis reaction from further conversion of the desired acetylene product to other compounds. Spray bars 75 may be used to introduce a quenching fluid, for example water or steam into the quench zone 72.

The reactor effluent exits the reactor via outlet 80 and as mentioned above forms a portion of the hydrocarbon stream. The effluent will include a larger concentration of acetylene than the feed stream and a reduced concentration of methane relative to the feed stream. The reactor effluent stream may also be referred to herein as an acetylene stream as it includes an increased concentration of acetylene. The acetylene stream may be an intermediate stream in a process to form another hydrocarbon product or it may be further processed and captured as an acetylene product stream. In one example, the reactor effluent stream has an acetylene concentration prior to the addition of quenching fluid ranging from about 2 mol-% to about 30 mol-%. In another example, the concentration of acetylene ranges from about 5 mol-% to about 25 mol-% and from about 8 mol-% to about 23 mol-% in another example.

The reactor vessel 10 includes a reactor shell 11. It should be noted that the term "reactor shell" refers to the wall or walls forming the reactor vessel, which defines the reactor chamber 15. The reactor shell 11 will typically be an annular structure defining a generally hollow central reactor chamber 15. The reactor shell 11 may include a single layer of material, a single composite structure or multiple shells with one or more shells positioned within one or more other shells. The reactor shell 11 also includes various zones, components, and or modules, as described above and further described below for the different zones, components, and or modules of the supersonic reactor 5. The reactor shell 11 may be formed as a single piece defining all of the various reactor zones and components or it may be modular, with different modules defining the different reactor zones and/or components.

As mentioned above, by one approach, the supersonic reactor 5 includes a quench zone 72 for effectively cooling the pyrolysis stream traveling therethrough. It should be noted that as used herein, "pyrolysis stream" may include one or all of the carrier stream, the feed stream, and the product effluent stream, before or during pyrolysis thereof.

In one approach, the quench zone 72 includes a spray quench system 75 for spraying a quench fluid into the quench zone to contact the pyrolysis stream and decrease the temperature thereof. The quench stream may include one or more of several different quench fluids. While a variety of quench fluids may be used in accordance herewith, by one approach, the quench fluid is selected to not interfere with the pyrolysis reaction other than cooling the pyrolysis stream. The quench fluid may also be selected so that it does not introduce a component into the pyrolysis stream which will contaminate a product thereof or cause difficulty in separating the component from a portion of the effluent stream. In this regard, in one example, the quench stream includes a component that is present in the process stream.

In one approach, the quench fluid includes cold water or steam. It should be noted that "cold" in reference to the quench stream is relative to the temperature of the pyrolysis stream, as the quench stream may still have an otherwise high temperature. In another approach, the quench fluid includes ethylene. In yet another approach, the quench fluid includes oil. It should be recognized, that these fluids will not substantially interfere with the pyrolysis reaction, other than decreasing the temperature to stop the reaction, and either form a desired part of the process stream or can be separated therefrom.

In another approach, the quench fluid includes chlorine. In this manner, upon introduction of the quench stream, the chlorine will react with acetylene in the pyrolysis stream to produce vinyl chloride, which may be a desired product.

Figure 3:
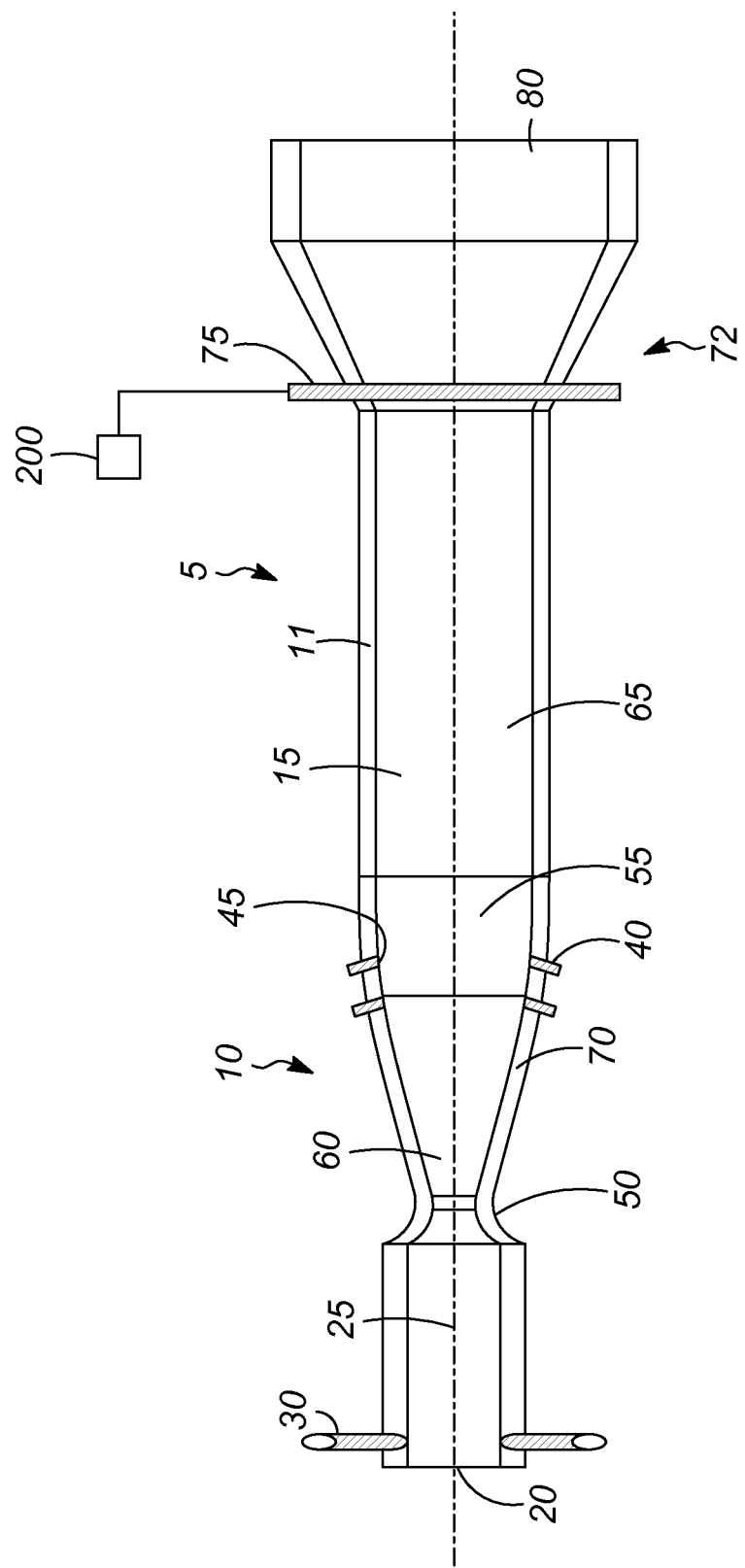
FIG. 3 is a side cross-sectional view of a supersonic reactor in accordance with various embodiments described herein.

In one approach, the quench system includes a quench fluid source 200 and at least one inlet 75, as illustrated in FIG. 3 for introducing the quench stream into the quench zone 72 of the reactor chamber 15 to quench the pyrolysis stream. In one approach, the inlet includes a nozzle. The nozzle may be configured to direct the quench fluid into the quench zone 72 to provide good mixing of the quench fluid with the pyrolysis stream and desired cooling of the pyrolysis stream.

As mentioned above, it has been identified that the high temperatures and flowrates, as well as other harsh operating conditions and components present within the reactor chamber 15 may cause melting and/or deterioration of the equipment and components of the quench system. More particularly, temperatures in the quench zone may, in one example, range from about 1100° C. to about 2500° C. In another example, temperatures in the quench zone may range from about 1200 to about 2000° C. In another example, temperatures in the quench zone may range from about 1300 to about 1800° C. The temperature of the hot fluid in the quench zone may be decreased at the outlet to less than about 1000° C. The temperature of the hot fluid is preferably reduced to 800° C. or less, and preferably to a temperature between 100° C. and 800° C., with a nominal target temperature of 250° C. Further, fluid velocity may be reduced in the quench zone, in one example, from about Mach 1.0 to Mach 3.0 to less than about Mach 0.5, with a preferred exit fluid velocity less than about Mach 0.1. Further, components in the pyrolysis stream may cause corrosion, oxidation, or reduction of equipment or components within the quench zone 72.

In this regard, the inlet according to one approach is formed to withstand these harsh operating conditions. While other types of inlets may be used, description will be provided for an inlet including a nozzle. In one approach, one or more portions of the nozzle are formed as a casting. Thus, by forming a portion of the reactor shell as a casting, a more isotropic microstructure is provided. The cast portion of the reactor shell may provide corrosion resistance over similar components formed by other methods, such as welding or forming. Forming the portion of the reactor shell from a casting may also provide better and more uniform high temperature creep and failure resistance than forming the shell by other methods.

By one approach, the casting may include a directional casting to provide improved thermal shock resistance and creep resistance at the elevated reaction temperatures and pressures. In one approach, the casting includes a columnar grain structure. In another approach, the casting includes a single crystal structure.

The casting may be formed from one or more materials as described further below. The cast portion of the reactor may be further treated by various methods known in the art. For example, the nozzle may be coated, as further described herein, heat treated, tempered, carbided, nitride, or treated in other known methods to improve its properties.

Thus, by forming a portion of the nozzle as a casting, a more isotropic microstructure is provided. The cast portion of the reactor shell may provide corrosion resistance over similar components formed by other methods, such as welding or forming. Forming the portion of the reactor shell from a casting may also provide better and more uniform high temperature creep and failure resistance than forming the shell by other methods.

By one approach, at least a portion of the nozzle 75 is constructed of a material having a high melting temperature to withstand the high operating temperatures of the quench zone 72. In one approach, one or more materials forming the portion of the nozzle 75 may have a long low-cycle fatigue life, high yield strength, resistance to creep and stress rupture, oxidation resistance, and compatibility with coolants and fuels. In one example, at least a portion of the nozzle 75 is formed of a material having a melting temperature of between about 800 and about 4000 C, and in another example from about 1200 to about 3500 C, and in yet another approach between about 1800 and about 3200 C. The materials may also exhibit microstructural stability through diverse thermal and mechanical processing procedures, compatibility with bonding processes and good adherence of oxidation resistant coatings. Some preferred materials for forming at least a portion of the nozzle 40 include superalloy alloys and nickel and gamma Ti aluminides. By one approach, the superalloy is a nickel based superalloy, and by another approach, the superalloy is an iron based superalloy.

In one approach, the at least portion of the nozzle is formed from a superalloy. In this regard, the nozzle construction may provide excellent mechanical strength and creep resistance at combustion and pyrolysis temperatures occurring within the reactor. In this manner, the nozzle may also restrict melting or failure due to the operating temperature along with the pressures in the quench zone 72.

According to another approach, the portion of the nozzle is formed from a material selected from the group consisting of a carbide, a nitride, titanium diboride, a sialon ceramic, zirconia, thoria, a carbon-carbon composite, tungsten, tantalum, molybdenum, chromium, nickel and alloys thereof.

According to yet another approach, the portion of the nozzle is formed from a material selected from the group consisting of the casting comprises a component selected from the group consisting of duplex stainless steel, super duplex stainless steel, and nickel-based high-temperature low creep superalloy.

Chromium or nickel may be included to provide good corrosion resistance.

By another aspect, the reactor walls are constructed of a material having high thermal conductivity. In this manner, heat from the reactor chamber 15 may be quickly removed therefrom. This may allow a skin temperature of an internal surface of the reactor shell 11 from being heated to temperatures at or near the reactor temperature, which may cause melting, chemical fire, or other deterioration, to the reactor shell 11 walls. In one example, the one or more portions of the reactor are formed from a material having a thermal conductivity of between about 200 and about 500 W/m-K. In another example, the thermal conductivity is between about 300 and about 450 W/m-K. In yet another example, the thermal conductivity is between about 200 and about 346 W/m-K, and may be between about 325 and 375 W/m-K in yet another example.

It has been found that according to this approach, the reactor shell may be formed from a material having a relatively low melting temperature as long as the material has a very high thermal conductivity. Because heat from the reaction chamber 15 is quickly removed in this approach, the reactor shell 11 is not exposed to as high a temperature. In this regard, the forming of the reactor shell portion from a material having a high thermal conductivity, the material may have a melting temperature below the temperature in the reactor chamber 15. In one example, the portion of the reactor shell 11 is formed from a material having a melting temperature of between about 500 and about 2000° C. In another example, the reactor shell 11 portion may be formed from a material having a melting temperature of between about 800 and about 1300° C. and may be formed from a material having a melting temperature of between about 1000 and about 1200° C. in another example.

By one approach, the material having a high thermal conductivity includes a metal or metal alloy. In one approach, one or more portions of the reactor shell 11 may be formed from copper, silver, aluminum, zirconium, hafnium, and their alloys. In this regard, it should be noted that one or more of the materials listed above may also be used to form a coating on a reactor shell substrate or to form a layer of a multilayer reactor shell 11. By one approach, the reactor shell 11 portion includes copper or a copper alloy. In one example, the reactor shell portion includes a material selected from the group consisting of copper chrome, copper chrome zinc, copper chrome niobium, copper nickel and copper nickel tungsten. In another example, the reactor shell portion comprises niobium-silver. In order to enhance the removal of heat from reactor chamber, cooling may be used to more quickly remove the heat from the reactor chamber so that a temperature thereof is maintained below and allowable temperature.

According to one approach, one or more components of the system 72 may be removed and replaced during operation of the supersonic reactor or during downtime thereof. For example, the quench nozzle may deteriorate more quickly than other components of the reactor, the nozzle may be removable so that it can be replaced with a new nozzle upon deterioration thereof. In one approach, the plurality of supersonic reactors, for example between 2 and 10, may be provided in parallel or in series with one or more supersonic reactors in operation and one or more supersonic reactors in standby so that if maintenance or replacement of one or more components of the operating supersonic reactor is required, the process may be switched to the standby supersonic reactor to continue operation.

In one example, the reactor effluent stream after pyrolysis in the supersonic reactor 5 has a reduced methane content relative to the methane feed stream ranging from about 15 mol-% to about 95 mol-%. In another example, the concentration of methane ranges from about 40 mol-% to about 90 mol-% and from about 45 mol-% to about 85 mol-% in another example.

In one example the yield of acetylene produced from methane in the feed in the supersonic reactor is between about 20 C-mol % and about 95 C-mol %. In another example, the yield of acetylene produced from methane in the feed stream is between about 40 C-mol % and about 90 C-mol %. Advantageously, this provides a better yield than the estimated 40% yield achieved from previous, more traditional, pyrolysis approaches. C-mol % is the carbon-mole % in the stream.

By one approach, the reactor effluent stream is reacted to form another hydrocarbon compound. In this regard, the reactor effluent portion of the hydrocarbon stream may be passed from the reactor outlet to a downstream hydrocarbon conversion process for further processing of the stream. While it should be understood that the reactor effluent stream may undergo several intermediate process steps, such as, for example, water removal, adsorption, and/or absorption to provide a concentrated acetylene stream, these intermediate steps will not be described in detail herein.

Referring to FIG. 2, the reactor effluent stream having a higher concentration of acetylene may be passed to a downstream hydrocarbon conversion zone 100 where the acetylene may be converted to form another hydrocarbon product. The hydrocarbon conversion zone 100 may include a hydrocarbon conversion reactor 105 for converting the acetylene to another hydrocarbon product. While FIG. 2 illustrates a process flow diagram for converting at least a portion of the acetylene in the effluent stream to ethylene through hydrogenation in hydrogenation reactor 110, it should be understood that the hydrocarbon conversion zone 100 may include a variety of other hydrocarbon conversion processes instead of or in addition to a hydrogenation reactor 110, or a combination of hydrocarbon conversion processes. Similarly, unit operations illustrated in FIG. 2 may be modified or removed and are shown for illustrative purposes and not intended to be limiting of the processes and systems described herein. Specifically, it has been identified that several other hydrocarbon conversion processes, other than those disclosed in previous approaches, may be positioned downstream of the supersonic reactor 5, including processes to convert the acetylene into other hydrocarbons, including, but not limited to: alkenes, alkanes, methane, acrolein, acrylic acid, acrylates, acrylamide, aldehydes, polyacetylides, benzene, toluene, styrene, aniline, cyclohexanone, caprolactam, propylene, butadiene, butyne diol, butandiol, C2-C4 hydrocarbon compounds, ethylene glycol, diesel fuel, diacids, diols, pyrrolidines, and pyrrolidones.

A contaminant removal zone 200 for removing one or more contaminants from the hydrocarbon or process stream may be located at various positions along the hydrocarbon or process stream depending on the impact of the particular contaminant on the product or process and the reason for the contaminants removal, as described further below. For example, particular contaminants have been identified to interfere with the operation of the supersonic flow reactor 5 and/or to foul components in the supersonic flow reactor 5. Thus, according to one approach, a contaminant removal zone is positioned upstream of the supersonic flow reactor in order to remove these contaminants from the methane feed stream prior to introducing the stream into the supersonic reactor. Other contaminants have been identified to interfere with a downstream processing step or hydrocarbon conversion process, in which case the contaminant removal zone may be positioned upstream of the supersonic reactor or between the supersonic reactor and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the hydrocarbon or process stream. In still other approaches, a contaminant removal zone may overlap or be integrated with another process within the system, in which case the contaminant may be removed during another portion of the process, including, but not limited to the supersonic reactor 5 or the downstream hydrocarbon conversion zone 100. This may be accomplished with or without modification to these particular zones, reactors or processes. While the contaminant removal zone 120 illustrated in FIG. 2 is shown positioned downstream of the hydrocarbon conversion reactor 105, it should be understood that the contaminant removal zone 120 in accordance herewith may be positioned upstream of the supersonic flow reactor 5, between the supersonic flow reactor 5 and the hydrocarbon conversion zone 100, or downstream of the hydrocarbon conversion zone 100 as illustrated in FIG. 2 or along other streams within the process stream, such as, for example, a carrier fluid stream, a fuel stream, an oxygen source stream, or any streams used in the systems and the processes described herein.

In one embodiment, the invention provides for a quench section for high temperature flows. The quench section has a frustum shape, an inlet at one end of the frustum, and outlet at the opposite end of the frustum, and a quench section wall. As used hereinafter, the term frustum indicates a regular polysided tubular structure, and can include a tubular structure with a circular cross-section. The frustum shape further includes the inlet cross-section as less than or equal to the outlet cross-section. The frustum is intended to include a cylindrical structure. The quench section further includes at least one nozzle embedded in the quench section wall, with the nozzles flush with the quench section wall. The inlet is at the first end of the frustum shaped quench section and the outlet is at the second end of the frustum shaped quench section. The second end has a cross-section greater than or equal to the cross-section of the first end. The quench section has a cross-section that is a regular polygon, and can include a circular cross-section. In one embodiment, the quench section can include two parts, a cylindrical part and a conic, or frustum shaped, part attached to the cylindrical part, wherein the smaller end of the conic part is attached to the cylindrical part.

Figure 4:
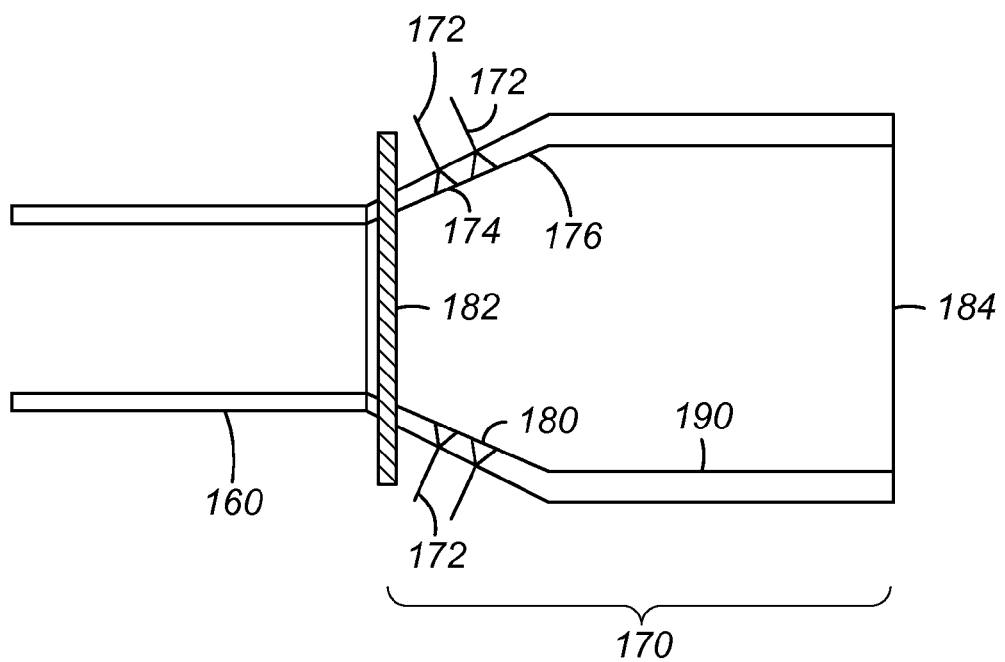
FIG. 4 is a side cross-sectional view of the quench section.
Figure 5:
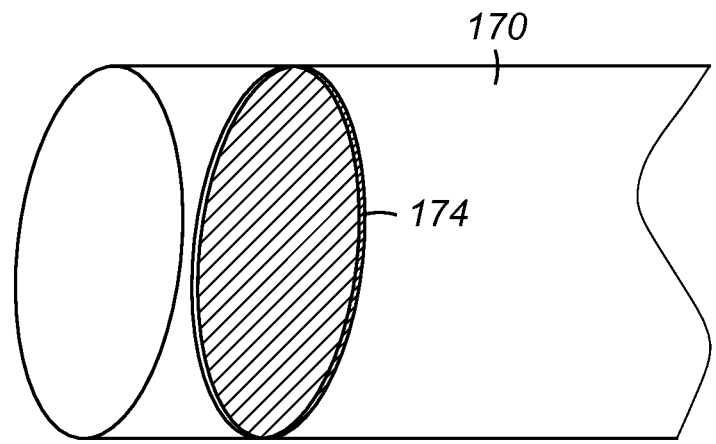
FIG. 5 is a perspective view of the overlapping slotted nozzles.
Figure 6:
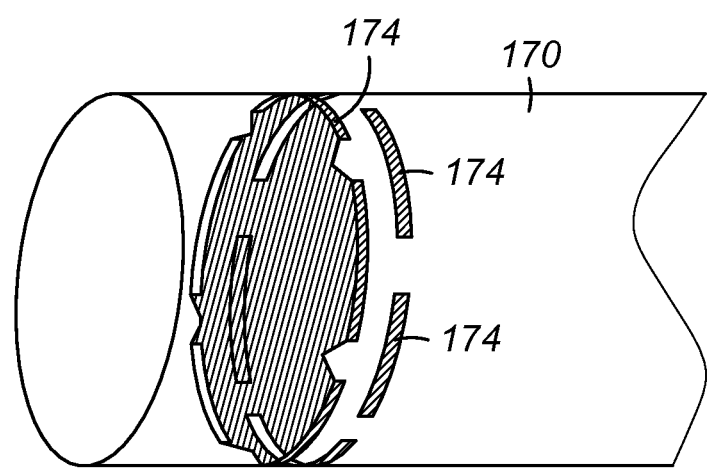
FIG. 6 is a perspective view of the continuous nozzle.

As shown in FIG. 4, the quench section 170 is in direct fluid communication with the reactor section 160. The quench section 170 includes at least one nozzle 172 having a nozzle outlet 174 that is flush with the quench section wall 176. In one embodiment, there are a plurality of nozzles 174. In another embodiment, the nozzle can have an outlet that is a continuous opening having a circumferential, or partial circumferential opening. FIGS. 5 and 6 show a section of the quench section 170 with nozzle outlets 174 having a continuous circumferential opening and several partial circumferential openings, respectively. FIG. 6 also includes an overlapping configuration of nozzle openings 174. For the embodiment, as shown in FIG. 6, the arc length of the nozzle openings 174 have an angle greater than 10 degrees around the quench section 170 circumference.

The quench section 170 is shaped and sized to meld smoothly with the reactor section 160 outlet. The quench section 170 has a cross-section that comprises a regularly shaped polygon having at least 6 sides. Preferably, the cross-section comprises a regular polygonal shape having at least 10 sides. In a most preferred embodiment, the quench section 170 has a cross-section having a circular shape.

The quench section 170 has a generally conical shape with a central axis. The quench section 170 includes a plurality of nozzles that lie in a plane that is perpendicular to the central axis, and the plurality of nozzles comprises at least 4 nozzles. In one embodiment, the plurality of nozzles comprises between 8 and 32 nozzles, evenly spaced around the circumference. The nozzles are spaced radially around the circumferences, and the spacing is between 15 and 45 degrees between neighboring nozzles for the case of 8 to 24 nozzles spaced around the circumference. A preferred spacing is between 20 and 25 degrees for 16 nozzles spaced around the circumference. In one embodiment, a very large number of nozzles can be spaced around the circumference with significantly overlapping sprays. Alternate nozzle arrangements are also contemplated, The choice and number will depend on considerations including design considerations, as well as physical limitations in the number of nozzles within a small space. The quench section 170 includes a first section 180 and a second section 190 wherein the first section 180 is affixed to the outlet of the reactor section 160, and the second section 190 is downstream of the first section 180 and affixed to the first section 180. The first section 180 can comprise the half of the quench section 170, or can comprise a smaller portion such as a quarter of the quench section 170. The nozzles 172 for dispersing the quench fluid are disposed within the first section 180 of the quench section 170.

The nozzles 172 can be a plurality of smaller nozzles spaced in a circumferential manner around the quench section 170, and substantially spaced equidistant from neighboring nozzles 172. One form of the plurality of nozzles can comprise a dense number of openings and can include a plurality of small discreet holes in a sheet over larger openings. The holes can be from a perforated sheet, a wire mesh, or a profile wire section.

In another embodiment, the quench section 170 includes at least two rows of nozzles, with each row of nozzles distributed circumferentially around the quench section wall 176. In one embodiment, each row is disposed within a circular section that is oriented in a plane perpendicular to the quench section central axis. While for a particular embodiment, the circular section can be perpendicular, this is not intended to be a limitation, but that the circumferentially distributed nozzles can be in a circumferential band that is at an oblique angle to the central axis, where oblique is intended to be an angle less than 90 degrees, but greater than 0 degrees relative to the central axis. For the embodiment comprising two rows, the nozzles in the second row are off-set relative to the positions of the nozzles in the first row. Preferably, the nozzles in the second row are offset to a position that is substantially located at an angle with respect to the central axis, half-way between neighboring nozzles in the first row.

The quench system includes spray nozzles 172 having a shaped orifice 174 for generating a spray having an angle between 30 degrees and 120 degrees. A preferred spray angle for the nozzles is an angle between 60 and 90 degrees. In one embodiment, the quench system utilizes spray nozzles that include an atomizer. The atomizer is for generating small quench fluid droplets to increase the rate of heat transfer between the quench fluid and the hot reaction gases by increasing the surface area of the quench fluid. One example of an atomizer is an ultrasonic atomizer.

The quench section 170 will have a cross-sectional area that either remains constant and/or increases in the direction of flow of the hot reaction gases and the quench fluid. In one embodiment, the quench system includes a quench section that has a ratio of the cross-sectional open area of the outlet 184 of the quench section to the cross-sectional open area of the inlet 182 of at least 1. In one embodiment, the ratio of the outlet 184 cross-sectional area to the inlet 182 cross-sectional area is at least 2, with a specific embodiment having a ratio between 3 and 6.

The quench section 170 is designed for rapid cooling and includes a selection of quench fluids sufficient to cool the reaction gases. The quench section 170 is also designed to have a length sufficient for the cooling to take place. The quench section has a length to inlet diameter ratio of at least 3 with an embodiment having the length to inlet diameter ratio between 5 and 10, with an alternate embodiment having a ratio between 3 and 6.

One embodiment of the present invention is a process for cooling a high speed vapor flow. The process includes passing the high speed vapor flow to a quench section. A liquid is sprayed into the quench section, wherein the quench liquid has a high heat of vaporization, and the liquid is sprayed into the quench section as droplets having a mean diameter less than 5000 micrometers, preferably less than about 1500 micrometers, and more preferably less than about 500 micrometers. The quench section comprises a frustum shape with an inlet and an outlet, and a quench section wall, and includes a plurality of spray nozzles embedded in the quench wall with the nozzles substantially flush with the quench section wall.

The process includes a high speed vapor flow that enters the quench section at a temperature of at least 1000° C., and where the temperature is generally going to be between 1300° C. and 1800° C. The temperature of the reaction gases will be reduced to a temperature less than about 1200° C., and preferably less than 1000° C., or more preferably to a temperature between 150° C. and about 800° C.

The quench fluid includes a high heat capacity liquid that is not reactive relative to acetylene. Quench fluids can include water, wet steam, chlorine, liquid hydrocarbons, and in particular liquid normal paraffins, and mixtures of these liquids. The quench process includes spraying the quench fluid in the first quarter section of the quench section, wherein the first quarter section comprises the first quarter of the axial length of the quench section as measured from the inlet to the quench section.

The process includes spraying the quench fluid through a plurality of nozzles disposed circumferentially around the quench section wall to deliver the quench liquid in substantially equal amounts from each nozzle. The spray nozzles are distributed around the circumference of the quench section, and are distributed in an array to substantially deliver the quench fluid in a substantially uniform into the quench section from around the circumference. The nozzles can be distributed in an region that forms a circular band around the quench section, or the nozzles can be distributed in a manner that forms an oblique band around the central axis of the quench section. In one embodiment, the quench fluid is delivered through two sets of nozzles, distributed circumferentially around the quench section wall, and where the nozzles are distributed within two circular sections of the quench section wall, and where each circular section is substantially perpendicular to the central axis of the quench section.

In one embodiment, the quench liquid is sprayed into the quench section in droplets having a mean diameter in the range from 10 micrometers to 500 micrometers, with a more common range from 50 micrometers to 500 micrometers, with a preferred droplet distribution having a mean diameter in the range from 70 micrometers to 200 micrometers. In another embodiment, the spray comprises an atomized spray and has a mean diameter in the range from 10 micrometers to 200 micrometers, and a preferred embodiment has a mean droplet diameter in the range from 20 micrometers to 100 micrometers. In one embodiment the spray is atomized with a gas. Gases that can be used include steam, nitrogen (N2), hydrogen (H2), or light hydrocarbon, such as C1 to C6 hydrocarbons.

The process is for cooling a high speed vapor flow where the vapor flow through the quench section inlet has a speed in the range from 10 m/s to 1000 m/s, with a nominal speed in the range of 10 m/s to 300 m/s and more commonly 20 m/s to 300 m/s. In a more controlled operation, the speed is in the range from 130 m/s to 210 m/s. The process includes a rapidly slowing vapor flow where the high speed vapor enters the quench section at a pressure between 100 kPa and 1 MPa absolute.

The quench liquid is sprayed into the quench section at a rate between 0.01 and 3 kg/s per kg of hot gas entering the quench section, with a preferred rate between 0.6 and 2 kg/s per kg of hot gas. The quench liquid is sprayed at conditions to provide for a Rosin-Rammler distribution of spray droplets, and the quench liquid is sprayed with a nozzle exit velocity between 10 m/s and 300 m/s, and preferably between 50 m/s and 150 m/s. The spray droplets must be sprayed at a sufficient velocity to enter the high speed vapor flow, but must also enter at a speed low enough to prevent all of the quench liquid penetrating to the center of the high speed vapor flow. The quench liquid is sprayed into the quench section with a momentum flux, where the momentum flux is between $2\times10^6$ N-s/(m$^2$-s) and $1\times10^8$ N-s/(m$^2$-s), where N is Newtons, m is meters, and s is seconds, with a preferred flux between $2\times10^6$ N-s/(m$^2$-s) and $3\times10^7$ N-s/(m$^2$-s). For water as a quench liquid with a density of 1 g/cc, and a nozzle exit velocity between 50 m/s and 150 m/s, this translates to a momentum flux from $2.5\times10^6$ N-s/(m$^2$-s) and $2.25\times10^7$ N-s/(m$^2$-s). When the quench liquid is sprayed with a gas assist atomization, the weight percent of gas in the spray is from 0.5% to 5%, with a preferred range between 1% and 2% of the weight of the atomization stream. During operation, with a front row of injectors and one or more back rows of injectors, where the front row is the row of injectors that first encounters the hot gas and the back rows are downstream of the front row, the momentum flux is preferred to be set at different rates. For the front row, the momentum flux is between $4\times10^6$ N-s/(m$^2$-s) and $8\times10^7$ N-s/(m$^2$-s), and for the back row, the momentum flux is between $3\times10^6$ N-s/(m$^2$-s) and $7\times10^7$ N-s/(m$^2$-s).

The quench liquid is injected into the system, and is more dense than the hot gas, although the hot gas will be traveling at a much higher speed. In one embodiment, the ratio of the momentum flux of the quench liquid to the hot gas entering the quench section is between 10 and 2000. In an embodiment with multiple rows of injectors, the front most, or upstream, row has a momentum ratio between 40 and 800, with the back row(s), or downstream row(s), having a momentum ratio between 30 and 700.

The quench liquid is sprayed into the quench section in an orientation toward the center of the quench section and to any angle (spray nozzle angle) between perpendicular to the central axis of the quench section and parallel to the central axis of the quench section. The quench liquid can also be sprayed substantially perpendicular to the quench section wall. The spray will have a spray angle between 30 degrees and 120 degrees, and preferably between 60 degrees and 90 degrees. This is the orientation relative to the spray having a central line directed toward the center of the quench section, or having a central line perpendicular to the wall of the quench section. In another embodiment, the spray nozzle angle of the quench liquid entering the quench section is at an oblique angle to the central axis of the quench section, and is at an angle between 0 degrees and 30 degrees, with an angle around 15 degrees desired, and with a spray angle between 30 and 90 degrees, and preferably around 60 degrees. In another embodiment, the spray nozzle angle of the quench liquid entering the quench section is at an oblique angle to the wall of the quench section, and is at an angle between 0 degrees and 30 degrees, with an angle around 15 degrees desired, and with a spray angle between 30 and 90 degrees, and preferably around 60 degrees. The spray angle is the spread of the spray exiting the nozzle, and the spray nozzle angle is the orientation of the spray nozzle for delivering the spray into the quench section.

Spray patterns for the quench section include a hollow flat fan spray, a solid flat fan spray, a hollow full cone spray, a solid full cone spray, a hollow partial cone spray, a solid partial cone spray, a hollow ellipse spray and a solid ellipse spray. A circumferential nozzle with generally have a spray nozzle angle perpendicular to the wall, but with the orientation of spray nozzle outlet walls, the spray nozzle angle can be adjusted to be non-perpendicular to the wall. A preferred pattern is a spray that is coming from a circumferential nozzle having an opening that completely follows the circumference of the quench section, and has a spray angle between 0 and 120 degrees, with a specific embodiment of a spray angle between 30 and 90 degrees.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the quenching of a high speed vapor flow, comprising:
    passing the high speed vapor flow to a quench section; and
    spraying a liquid into the quench section, wherein the liquid has a high heat of vaporization, and the liquid is sprayed into the quench section with droplets having a mean diameter less than 500 micrometers;
    wherein the quench section comprises a frustum shape with an inlet, an outlet, and quench section wall; and
    a plurality of nozzles embedded in the quench wall with the nozzles substantially flush with the quench section wall.

2. The process of claim 1 wherein the high speed vapor flow enters the quench section at a temperature of at least 1000° C.

3. The process of claim 2 wherein the high speed vapor flow enters the quench section at a temperature between 1000° C. and 2500° C.

4. The process of claim 1 wherein the quench liquid is a not reactive liquid relative to acetylene.

5. The process of claim 4 wherein the quench liquid is selected from the group consisting of water, wet steam, liquid hydrocarbons, and mixtures thereof.

6. The process of claim 1 wherein the quench section comprising a frustum has a first quarter section beginning at the quench section inlet and extending to one quarter the axial length from the quench section inlet to the quench section outlet, wherein the spraying liquid is sprayed into the high speed vapor flow in the first quarter section.

7. The process of claim 1 wherein the spraying is performed by a plurality of nozzles disposed circumferentially around the quench section wall to deliver the quench liquid in a substantially equal amounts from each nozzle.

8. The process of claim 1 wherein the quench section has a central axis, and the plurality of nozzles are distributed circumferentially in a first row around the quench section wall, and are disposed within two circular sections where each circular section is oriented at an angle between 0 and 120 degrees to the quench section central axis, and wherein the spraying of the quench liquid is delivered to the quench section in the two regions.

9. The process of claim 8 wherein a second row of nozzles has an orientation at an angle relative to the central axis less than the orientation angle for the first row of nozzles.

10. The process of claim 1 wherein the spraying liquid is delivered into the quench section with droplets having a mean diameter in the range from 50 micrometers to 500 micrometers.

11. The process of claim 10 wherein the spraying liquid is delivered into the quench section with droplets having a mean diameter in the range from 70 micrometers to 200 micrometers.

12. The process of claim 1 wherein the spraying liquid is delivered into the quench section through atomization and the droplets are delivered with a mean diameter in the range from 10 micrometers to 200 micrometers.

13. The process of claim 12 wherein the spraying liquid is delivered into the quench section through atomizing with a gas and the droplets are delivered with a mean diameter in the range from 25 micrometers to 100 micrometers.

14. The process of claim 1 wherein the high speed vapor flow entering the quench section is in the range of 100 m/s to 1000 m/s.

15. The process of claim 1 wherein the high speed vapor flow enters the quench section at a pressure between 100 kPa to 1 MPa.

16. The process of claim 1 wherein the quench liquid is sprayed to the quench section at a rate between 0.1 kg/s and 2 kg/s per kg of gas entering the quench section.

17. The process of claim 1 wherein the quench liquid is sprayed at conditions to provide a Rosin-Rammler distribution of spray droplets.

18. The process of claim 1 wherein the quench liquid has a nozzle exit velocity between 10 m/s and 200 m/s.

19. The process of claim 1 wherein the quench liquid has a momentum flux between $2\times10^6$ N-s/(m$^2$-s) and $3\times10^7$ N-s/(m$^2$-s).

20. The process of claim 1 wherein the ratio of the momentum flux of the quench liquid to the hot gas entering the quench section is between 20 and 1000.

* * * * *